(12) United States Patent
Flood

(10) Patent No.: US 9,649,342 B2
(45) Date of Patent: *May 16, 2017

(54) REGENERATION OF SPINAL DISCS

(71) Applicant: Laser Spine Institute, LLC, Tampa, FL (US)

(72) Inventor: Mark Flood, St. Petersburg, FL (US)

(73) Assignee: Laser Spine Institute, LLC, Tampa, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/699,349

(22) Filed: Apr. 29, 2015

(65) Prior Publication Data

US 2015/0246077 A1 Sep. 3, 2015

Related U.S. Application Data

(63) Continuation of application No. 13/762,471, filed on Feb. 8, 2013, now Pat. No. 9,114,190.

(51) Int. Cl.
| | |
|---|---|
| *A61K 35/28* | (2015.01) |
| *A61K 35/32* | (2015.01) |
| *A61K 35/19* | (2015.01) |
| *A61L 27/38* | (2006.01) |
| *A61K 35/35* | (2015.01) |
| *A61K 35/30* | (2015.01) |
| *A61L 27/36* | (2006.01) |
| *A61K 38/18* | (2006.01) |
| *A61K 38/30* | (2006.01) |
| *A61K 38/39* | (2006.01) |
| *A61K 35/18* | (2015.01) |
| *A61K 35/16* | (2015.01) |
| *A61K 38/19* | (2006.01) |
| *A61K 38/48* | (2006.01) |

(52) U.S. Cl.
CPC .............. *A61K 35/35* (2013.01); *A61K 35/16* (2013.01); *A61K 35/18* (2013.01); *A61K 35/19* (2013.01); *A61K 35/28* (2013.01); *A61K 35/30* (2013.01); *A61K 35/32* (2013.01); *A61K 38/1858* (2013.01); *A61K 38/1875* (2013.01); *A61K 38/19* (2013.01); *A61K 38/30* (2013.01); *A61K 38/39* (2013.01); *A61K 38/4833* (2013.01); *A61L 27/3658* (2013.01); *A61L 27/3817* (2013.01); *A61L 27/3834* (2013.01)

(58) Field of Classification Search
None
See application file for complete search history.

(56) References Cited

U.S. PATENT DOCUMENTS

| | | |
|---|---|---|
| 6,340,369 B1 | 1/2002 | Ferree |
| 7,121,996 B2 | 10/2006 | Hancher et al. |
| 7,858,296 B2 | 12/2010 | Sowemimo-Coker et al. |
| 2002/0161449 A1 | 10/2002 | Muschler |
| 2004/0088053 A1 | 5/2004 | Serhan et al. |
| 2004/0120942 A1* | 6/2004 | McGinnis .......... A61K 38/4833 424/94.64 |
| 2004/0199043 A1 | 10/2004 | Hancher et al. |
| 2005/0149046 A1 | 7/2005 | Friedman et al. |
| 2006/0036299 A1 | 2/2006 | Anders et al. |
| 2010/0028309 A1 | 2/2010 | Odar et al. |
| 2012/0068085 A1 | 3/2012 | Cucin |
| 2012/0101479 A1 | 4/2012 | Paspaliaris et al. |
| 2012/0197320 A1 | 8/2012 | Berecski |

FOREIGN PATENT DOCUMENTS

| | | |
|---|---|---|
| WO | 2005049055 A1 | 6/2005 |
| WO | 2008034803 A1 | 3/2008 |
| WO | 2012125899 A1 | 9/2012 |

OTHER PUBLICATIONS

International Search Report and Written Opinion, PCT/US14/14404, May 14, 2014.
Richardson, et al., Stem Cells, 2006, vol. 24, pp. 707-716.

* cited by examiner

*Primary Examiner* — Allison Fox
(74) *Attorney, Agent, or Firm* — Dorf & Nelson LLP; Scott D. Locke, Esq.

(57) ABSTRACT

Compositions and processes for the effective and efficient regeneration of spinal discs are provided. These compositions contain stem cells, donor cells, and platelet plasma compositions. By using these compositions, there is an increased likelihood of acceptance and proper cell differentiation.

5 Claims, No Drawings

REGENERATION OF SPINAL DISCS

FIELD OF THE INVENTION

The present invention relates to the field of regeneration of spinal discs.

BACKGROUND OF THE INVENTION

One of the major causes of back pain and disability is degeneration of lumbar intervertebral discs. This source of pain may affect up to 80% of Americans over the course of their lifetimes. Furthermore, the economic impact of treating persons who suffer from disc degeneration is over $20 billion per year. Thus, disc degeneration has a significant effect on a sizeable portion of the population.

Disc degeneration may begin in childhood as cells within an intervertebral disc that produce the substrates that maintain disc hydration undergo normal senescence. At approximately the time that a person is four years old, his or her notochord cells are lost permanently, and their function is replaced by cells called chondrocytes. Both chondrocytes and notochord cells produce proteoglycans; however, chondrocytes also produce significant amounts of collagen, thereby causing discs to become less hydrated and firmer. This physiologic event marks the onset of disc degeneration.

Disc degeneration may be accelerated by several factors, including but not limited to injury and aging. Ideally, discs would regenerate on their own. Unfortunately, the intervertebral discs of the spine often fail to heal from injury and aging because of a paucity of blood vessels. The lack of a robust blood supply causes the intervertebral discs to obtain nutrition and to eliminate waste through the process of imbibition, which is the displacement of one fluid by another fluid that is immiscible. Over time, this process causes a lower pH to develop in the intervertebral discs and homeostasis via imbibition cannot be sustained.

When there is disc degeneration, patients can experience significant pain, and researchers and clinicians have long sought methodologies for treating this pain. One of the common historical approaches has been spinal fusion, which is the joining of two or more vertebrae. Spinal fusion addresses the degenerating disc by excision of the disc and subsequently, either fusing the spine with bone products or replacing the excised disc with a mechanical device.

Unfortunately, spinal fusions can cost between $60,000 and $100,000 per patient and can be associated with complications at twice the rate of complications that accompany nerve decompression surgery, which is another method for treating pain. Additionally, the result of spinal fusion surgery is a shift of mechanical stress to the intervertebral disc level above and/or below the fused or replaced disc. This common phenomenon is known as adjacent level disease/degeneration, and it too can contribute to discomfort in a patient. A further challenge for treating compromised discs by the common methods used by practitioners is that these methods are primarily non-biologic in nature, and thus face challenges in being accepted by the recipient.

Because of the high costs that are associated with lumbar fusions along with inconsistent outcomes and higher complication rates, researchers and clinicians have developed biologic and other non-fusion approaches for treating disc degeneration. Current non-fusion approaches for treating a degenerating disc include stabilizing the disc, rehydrating the disc, rebalancing the pH in the disc, intradiscal injections, provision of extracellular matrix proteins, intradiscal pressure reduction, disc denervation, disc nucleus replacement, stimulation of disc chondrocyte proliferation, non-ablation laser treatment and stem cell therapy. However, none of these strategies as currently employed provide optimally effective and efficient means for treating degenerated discs. Thus, there is a need to develop new means by which to address disc degeneration.

SUMMARY OF THE INVENTION

The present invention provides compositions for treating degenerated spinal discs, as well as processes for making and using these compositions. Through the use of various embodiments of the present invention, one can increase the ability of discs to be regenerated and thereby reduce pain in patients who suffer from disc degeneration.

According to a first embodiment, the present invention is directed to a composition for regenerating a disc. The composition comprises: (a) stem cells from a subject; (b) donor disc cells, wherein the donor disc cells are derived from a non-degenerative level of a spine of the subject; and (c) a platelet plasma composition. In some embodiments, the donor disc cells are chondrocytes. Additionally, in some embodiments, the composition further comprises one or more of an extra-cellular matrix that, for example, may be derived from the non-degenerative level of the spine, growth factors such as platelet-derived growth factors, calcium chloride or a combination of calcium chloride and thrombin.

Optionally, prior to forming the composition for disc regeneration, one may morselize and/or extrude the chondrocytes. Further, prior to forming the composition for disc regeneration, one may concentrate or hemoconcentrate bone marrow aspirate to form a solution containing the stem cells and/or concentrate or hemoconcentrate the entire composition. The term "composition" means any combination of two or more substances, including, but not limited to, a mixture, a suspension, or a solution.

Furthermore, in some embodiments, the composition for disc regeneration is photoactivated. For example, it may be incubated under visible light wavelengths in order to increase the efficiency of the differentiation of the stem cells.

According to a second embodiment, the present invention is directed to a process for creating a composition for disc regeneration. The process comprises: (a) morselizing donor disc material, wherein the donor disc material comprises healthy cells obtained from a non-degenerative level of a spine; (b) extruding the donor disc material to form an extruded material that comprises chondrocytes and an extra-cellular matrix; and (c) mixing the chondrocytes, the extra cellular matrix, a bone marrow aspirate and a platelet plasma composition, wherein the platelet plasma composition comprises growth factors to form a composition for disc regeneration.

According to a third embodiment, the present invention is directed to a process for regenerating a disc. The process comprises: (a) harvesting bone marrow from a person; (b) generating bone marrow aspirate and a platelet plasma composition from the bone marrow, wherein the bone marrow aspirate comprises mesenchymal stem cells, plasma, platelets and red blood cells; (c) harvesting disc chondrocytes and an extra cellular matrix from non-degenerative disc tissue of the person; and (d) combining the bone marrow aspirate and the disc chondrocytes to form a composition under conditions that permit the mesenchymal stem cells to begin differentiation.

According to a fourth embodiment, the present invention provides a method for treating disc degeneration comprising administering a composition of the present invention to a person in need thereof. Preferably, a person of ordinary skill in the art will administer a therapeutically effective amount of the composition.

According to a fifth embodiment, the present invention provides a method treating disc degeneration comprising administering a composition made by a process of one or more of the embodiments of the present invention and further comprising: (a) mechanically decompressing the recipient disc; and (b) injecting the mixture into the recipient disc. The injection may be into the disc nucleus pulposus and/or into the posterior/posterolateral annulus fibrosus. Optionally, prior to injecting the mixture one may apply a low level laser treatment to the recipient disc.

Additionally, in various embodiments, a material for forming a scaffold may be used. This material may for example comprise bone marrow aspirate, a platelet plasma composition from the bone marrow and a coagulant that is made from $CaCl_2$ and thrombin. One may combine the scaffolding material with the composition prior to administration, or one may apply it to the site of interest after the composition is applied, or one may apply it to the site of interest prior to application of the composition.

DETAILED DESCRIPTION OF THE INVENTION

Reference will now be made in detail to various embodiments of the present invention. In the following detailed description, numerous specific details are set forth in order to provide a thorough understanding of the present invention. However, unless otherwise indicated or implicit from context, the details are intended to be examples and should not be deemed to limit the scope of the invention in any way.

According to one embodiment, the present invention is directed to a composition for regenerating a disc in need thereof. The disc that needs regeneration may be referred to as a "target disc." The target disc may be in need of regeneration because of degeneration due to aging or trauma or a combination thereof and may or may not be a source of pain for a patient. Alternatively or additionally, it may be in need of regeneration because of herniation. As persons of ordinary skill in the art will recognize, a target disc may be partially or completely degenerated.

The composition for regeneration may, for example, comprise, consist essentially of or consist of stem cells, donor disc cells, and a platelet plasma composition. The components may be combined prior to administration to a site of interest (i.e., the target disc) or they may be combined at the site of interest. When the composition is formed prior to introduction into a patient, it may be in the form of a medicament for use in treating disc degeneration. In some embodiments, all of the stem cells, the donor disc cells and the platelet plasma composition are derived from the same subject. In other embodiments, only the stem cells and the donor disc cells are derived from the same subject. The subject may, for example, be a human or other mammal, and preferably is the patient in need of disc regeneration.

Stem Cells

Stem cells are cells that have the capability to differentiate into a plurality of different types of cells. Thus, they can be replacement cells or a source of replacement cells, and they are capable of replacing cells that die due to injury, illness or disease. Cell death is referred to as senescence.

The path of differentiation that stem cells take is strongly influenced by cell-to-cell signaling. If stem cells are placed in a muscle, they can differentiate into muscle cells. If stem cells are placed in a tendon, they can differentiate into tendon cells. If one engrafts mesenchymal stem cells into a disc, the mesenchymal stem cells will differentiate into chondrocytes. However, if one were to place stem cells directly into an environment in which there is already degeneration, there is a significant likelihood that they would develop into degenerative type cells. Accordingly, and as discussed in more detail below, in various embodiments of the present invention one exposes stem cells to donor disc cells that are from a non-degenerative layer of the spine prior to injecting the stem cells into a target site. Preferably, both the stem cells and the donor disc cells are from the same subject.

Various embodiments of the present invention use stem cells for one or more the following purposes: (1) to stimulate natural disc regeneration; (2) to reduce inflammation within an intervertebral disc, epidural space and/or facet joint; (3) to provide replacement cells for senescent intervertebral disc cells; (4) to replenish an extracellular matrix; (5) to reduce pain; (6) to restore/maintain intervertebral disc height; (7) to stabilize intervertebral discs; and (8) to attract additional stem cells through chemotaxis.

Examples of stem cells that may be used in connection with the present invention are those that are derived from bone-marrow as well as those that are derived from adipose tissue, (e.g., subcutaneous fat), synovial fluid, peripheral blood, and amniotic fluid or amniotic membrane. The composition for regeneration may contain stem cells from any of these individual sources or from any plurality of these sources. Preferably the mesenchymal stem cells that are used are autologous. The term "autologous" means being derived from the same individual's body into which they will be transferred. By being autologous, there is a significantly reduced risk of rejection.

As persons or ordinary skill in the art know, within human bone marrow, there are a number of different types of blood cells, including mesenchymal stem cells. These cells are multipotent and can differentiate into a variety of cell types, including osteoblasts, chondrocytes and adipocytes. When obtaining mesenchymal stem cells from the bone marrow, one may directly remove a quantity of bone marrow into various size syringes that contain a pre-measured amount of anticoagulant. In some embodiments, 20-2000 cc or 50-1000 cc or 60-500 cc of bone marrow per ilium is extracted from the pelvis or 20-500 cc or 30-250 cc or 50-100 cc of bone marrow is retrieved per side of vertebrae. Examples of anticoagulants include but are not limited to EDTA, citrate, oxalate, ACD (acid citrate dextrose, which also may be referred to as anticoagulant citrate dextrose) in the form of ACD-A or ACD-B and heparin, which may be used in pre-coated syringes. By way of a non-limiting example, the volume of bone marrow may be between eight and ten times the volume of the anticoagulant, e.g., 54 cc of bone marrow and 6 cc of ACD-A.

In some embodiments, ultimately between 2 cc and 6 cc or between 3 cc and 5 cc or between 3.5 cc and 4.5 cc of BMAC is inserted to regenerate a disc. As persons of ordinary skill in the art will recognize the exact volume will depend on the size of the disc in need of regeneration or healing, which in part depends on the size of the patient.

After removal of the bone marrow, one may subject the contents of the syringe to centrifugation, thereby stratifying the bone marrow into specific blood tissue layers, e.g., bone marrow aspirate concentrate (BMAC) and a platelet plasma composition. The mesenchymal stem cells, which are part of the BMAC may then be removed for use in various embodiments of the present invention. Processes for removing products by centrifugation are well known to persons of ordinary skill in the art.

As noted above, stem cells may also be derived from adipose tissue. Human adipose tissue is a well-vascularized tissue, and the network of blood vessels that are integrated throughout subcutaneous fat is surrounded by numerous types of regenerative cells. These regenerative cells include mesenchymal stem cells as well as other cells that are important for tissue healing and regeneration such as monocytes and fibroblasts.

Cells that are positioned around the blood vessels in adipose tissue are commonly referred to as pericytes. The fraction of regenerative pericytes in adipose tissue is known as the stromal vascular fraction (SVF).

In order to obtain adipose tissue, one may harvest fat from the abdomen or the flank. After harvesting, one may separate SVF from the cells. By way of non-limiting examples, one may isolate SVF from the fat cells utilizing ex vivo ultrasonic cavitation, in vivo mechanical separation, collagenase digestion or lecithin emulsification. When isolating the SVF, one may spin down the material in order to obtain a pellet. Preferably, the pellet is substantially free of collagen.

By looking to adipose tissue for mesenchymal stem cells, one is able to yield a greater amount of mesenchymal stem cells than one is able to obtain from bone marrow. This benefit of using adipose tissue may be realized regardless of the age of the person from whom the tissue is obtained. Thus, in some embodiments, one may use stem cells exclusively from bone marrow, exclusively from fat tissue or stem cells from a combination thereof. When stem cells from a plurality of sources are used in the same composition, one may use them in approximately equal volume or in substantially unequal volumes, for example, 40-60% of each source or in substantially unequal volumes of 20-40% of adipose derived stem cells and 60-80% of bone marrow derived stem cells or 60-80% adipose derived stem cells and 20-40% of bone marrow derived stem cells. In one non-limiting example, a person of ordinary skill in the art may combine a pellet or ½ of a pellet of stem cells from adipose tissue with a volume of 1 cc-5 cc or 3 cc-5 cc or 1.5 cc-3 cc of BMAC.

Donor Disc Cells: Disc Chondrocytes

Donor disc cells are cells that are derived from a disc that is non-degenerative. The term "non-degenerative" means that it is not a site that is to be regenerated. Preferably, there is no degeneration or no degeneration beyond the minimal amount due to normal aging. A non-degenerative site may also be defined as a site with less degeneration than a site to which stem cells will be introduced.

In various embodiments of the present invention, the donor disc cells serve one or more, if not all, of the following purposes: (1) to provide non-degenerative intradiscal cells for autologous mesenchymal stem cells for socialization/differentiation; (2) to reduce inflammation within the intervertebral disc; (3) to provide replacement cells for senescent intervertebral disc cells; (4) to replenish extracellular matrix; (5) to reduce pain; (6) to restore/maintain intervertebral disc height; (7) to stabilize intervertebral discs; (8) to attract additional stem cells through chemotaxis; and (9) to add a biologic scaffold.

In order to obtain donor disc cells, one may introduce a guide wire into a site at which to harvest using fluoroscopic x-rays for guidance. One may then make an incision and use a retractor or cannula. The guide wire is removed, and one may then harvest donor disc material that comprises the donor disc cells. Examples of tools that may be used to harvest these materials include but are not limited to, an endopituitary tool, a water jet, a suction punch or other mechanical means. One may harvest the donor disc material from the nucleus pulposus and/or annulus fibrosis. Examples of sites from which to obtain donor disc material include but are not limited to the sacral level (S1/2), the thoracic level, the lumbar level, the stress shielded normal variant disc and a non-degenerative part of the treatment level. By way of a non-limiting example, in order to regenerate a disc, one may extract approximately 1-100 or 2-50 or 2-20 or 5-10 pieces of donor disc material that each are between 0.5-10 $mm^3$ or 0.5-2 $mm^3$ (e.g., approximately 1 $mm^3$) in size, and morselize them down to smaller sized pieces to put into discs. The smaller pieces may comprise, consist essentially of or consist of single cells or small clumps of cells, protein strands and connective tissue.

In some embodiments, the donor disc material is processed prior to mixing with the stem cells. For example, one may morselize the donor disc material in order to increase the surface area for contacts between stem cells and normal discs. Morselization will also expand the volume of normal extracellular matrix, which is part of the retrieved donor disc material. Methods for morselizing may, for example, employ a scalpel, a water jet and a morselizer.

Following or instead of morselization, the donor disc material may be subjected to extrusion. Extrusion frees chondrocytes from their surrounding matrix (e.g., an extracellular matrix, which is also referred to as ECM, and contains the interstitial matrix and the basement membranes). As with morselization, extrusion increases the cell surface in order to optimize contact between stem cells and normal disc cells.

In one non-limiting example, the extrusion process is accomplished through the use of two syringes and a connector. The connector has a smaller bore than the syringes. When the donor disc material is sent back and forth between the syringes, turbulence is created. The turbulence forces cells away from the other components of the tissue and can, in some embodiments, break cells apart.

Platelet Plasma Composition

The platelet plasma composition comprises, consists essentially of, or consists of platelets and plasma and may be derived from bone marrow or peripheral blood. The present invention may use platelet plasma compositions from either or both of these sources, and either platelet plasma composition may be used to regenerate either a nucleus or annulus in need thereof. Further, the platelet plasma composition may be used with or without concentrated bone marrow (BMAC). By way of example, when inserted into the annulus, 0.05-2.0 cc of platelet plasma composition may be used, and when inserted into the nucleus, 0.05-3.0 cc of the platelet plasma composition may be used.

Platelets are non-nucleated blood cells that as noted above are found in bone marrow and peripheral blood. They have several important functions such as controlling bleeding and tissue healing. As persons of ordinary skill in the art are aware, the ability to promote tissue healing is due to the many growth factors that they produce including platelet-derived growth factor (PDGF), transforming growth factor beta (TGF-beta), fibroblast growth factor (FGF), insulin-like growth factor-1 (IGF-1), connective tissue growth factor (CTGF) and vascular endothelial growth factor (VEGF).

Many of these platelet proteins and molecules are cytokines and are important for cell signaling and immunomodulation.

In various embodiments of the present invention, the platelet plasma composition may be obtained by sequestering platelets from whole blood or bone marrow through centrifugation into three strata: (1) platelet rich plasma; (2) platelet poor plasma; and (3) fibrinogen. When using platelets from one of the strata, e.g., the platelet rich plasma (PRP) from blood, one may use the platelets whole or their contents may be extracted and concentrated into a platelet lysate through a cell membrane lysis procedure using thrombin and/or calcium chloride. When choosing whether to use the platelets whole or as a lysate, one may consider the rate at which one desires regeneration and/or tissue healing (which may include the formation of scar tissue without regeneration or healing of a herniated or torn disc). In some embodiments the lysate will act more rapidly than the PRP (or platelet poor plasma from bone marrow).

Notably, platelet poor plasma that is derived from bone marrow has a greater platelet concentration than platelet poor rich plasma from blood. "PP/RP" (or "PPP") may be used to refer to platelet poor plasma derived from bone marrow, and in some embodiments, preferably PP/RP is used or PRP is used as part of the composition for disc regeneration. (By convention, the abbreviation PRP refers only to compositions derived from peripheral blood and PPP (or PP/RP) refers to compositions derived from bone marrow.)

In various embodiments, the platelet plasma composition, which may or may not be in the form of a lysate, may serve one or more of the following functions: (1) to release/provide growth factors and cytokines for tissue regeneration; (2) to reduce inflammation; (3) to attract/mobilize cell signaling; (4) to initiate fibroblast repair of damaged annulus through fibroblast growth factors (FGF); (5) to stabilize disc annulus; (6) to repair annulus disc tears; (7) to stimulate revascularization to a disc; and (8) to stimulate stem cell activation. Additionally, by combining platelet therapy with stem cells, there can be synergy with respect to reducing back pain.

In some embodiments in which the lysate is used, the cytokines are concentrated in order to optimize their functional capacity. Concentration may be accomplished in two steps. First, blood may be obtained and concentrated to a volume that is 5-15% of what it was before concentration. Devices that may be used include but are not limited to a hemofilter or a hemoconcentrator. For example, 60 cc of blood may be concentrated down to 6 cc. Next, the concentrated blood may be filtered to remove water. This filtering step may reduce the volume further to 33%-67% (e.g., approximately 50%) of what it was prior to filtration. Thus, by way of example for a concentration product of 6 cc, one may filter out water so that one obtains a product of approximately 3 cc.

When the platelet rich plasma, platelet poor plasma and fibrinogen are obtained from blood, they may for example be obtained by drawing 20-500 cc of peripheral blood, 40-250 cc of peripheral blood or 60-100 cc of peripheral blood. The amount of blood that one should draw will depend on the number of discs that have degenerated and the size of the discs. As persons of ordinary skill in the art will appreciate, a typical disc has a volume of 2-5 cc or 3-4 cc.

By way of non-limiting example, for a given disc, one may use a composition that comprises, consists essentially of or consists of ½-1 cc of PPP, 3-5 cc of BMAC and 10 mm$^3$ donor disc cells.

Composition for Regeneration

In some embodiments, prior to injecting the stem cells into the degenerative disc, one mixes them with donor disc cells for approximately 10-40 minutes or 20-40 minutes. In some embodiments, the stem cells are part of the BMAC at the time of combination. Additionally, preferably mixing is accompanied by warming.

Next, one may mix the donor disc cells and ECM with BMAC (if not already present or optionally with more BMAC if already present) and the platelet plasma composition, which preferably comprises growth factors. By mixing the donor disc cells with stem cells, one may initiate stem cell differentiation down a chondrocyte cell line through socialization, due to cell-to-cell signaling. The growth factors may, for example, be those identified elsewhere in this disclosure or that are now known or that come to be known to persons of ordinary skill in the art and that would be recognized as of use in connection with the present invention. Furthermore, the mixture may contain calcium chloride or both calcium chloride and thrombin to release growth factors. Mixing may be accomplished through the use of mechanical devices that are designed to permit mixing of the aforementioned materials, and be done at room temperature or warmed to a temperature greater than room temperature, but below which undesirable denaturation of proteins would occur. Optionally, it may also be activated under light.

Photoactivation

In some embodiments, one photoactivates the concentrated BMAC and donor chondrocytes. Optionally, this mixture also contains PP/RP or PRP at the time of photoactivation. Photoactivation may be carried out by a monochromatic light source, and photoactivation may take place prior to or after introducing the stem cells to the site of interest for a period of 10 minutes to 2 hours or 15 minutes to 1 hour or 20 minutes to 40 minutes.

In some embodiments, one carries out photoactivation under a wavelength of 390 nm-900 nm or 390 nm-600 nm, or 600 nm-900 nm or 600 nm-750 nm. Photoactivation may reduce pain, promote healing and/or increase the ability of stem cells to differentiate. In some embodiments, the mixture is incubated after it contains all ingredients but prior to administration. For example, one may use an Adi-Light or Adi-Light 2. Photoactivation increases the presence of the Interleukin-1 Receptor Antagonist (IL-1RA), which decreases the pain and inflammation associated with injections.

Target Site

The target site is the disc location at which there is degeneration and/or herniation. Optionally, prior to introduction of the stem cells, one decompresses the discs at the target site, which may also be known as the recipient disc. This may, for example, be accomplished by mechanical means. In order to cause mechanical decompression, one may, for example, use an endopituitary tool. Decompression both produces relief of pressure and creates space for the composition for regeneration and/or channels for rehydration.

Laser Therapy

In various embodiments of the present invention, one may also use laser therapy. The laser may, for example, be used to treat the nucleus pulposus of a disc of interest, and the process of using the laser may be referred to as photostimulation. When employing laser therapy one may, for example, use a Holmium:YAG; Nd:YAG; and/or Erbium:YAG laser light at non-ablation settings. By using the laser treatment at non-ablation settings one can stimulate chondrocyte proliferation and disc rehydration by a plurality of methods.

First, the non-ablation laser generator settings result in only low-level heat production and not thermal ablation of the disc. Thus, the low level heat production is able to stimulate chondrocyte proliferation without significant protein denaturation. Additionally, the non-ablation settings of the laser have the ability reduce volume and directionally bend or shrink cartilage, thereby effectively reducing the volume of a bulging disc. This benefit allows reduction of a bulging disc away from any juxtaposed spinal nerves.

Second, the non-ablation settings also allow one to form temperospatial bubbles or waves that create micro and nano pores due to the mechanical nature of their rapid formation and resolution. These micro and nano pores increase water permeability and thus, aid disc rehydration and the flow of nutrients.

Finally, the direct mechanobiologic effect of the temperospatial bubbles or waves particularly when the laser is in pulse mode, stimulates disc chondrocyte proliferation and production of new cartilage.

Injection of Stem Cells/Disc Chondrocytes/PP/RP and Scaffold to Treat Disc Nucleus After photoactivation, one may inject the composition for regeneration into several areas of the disc nucleus pulposus and/or into the posterior/posterolateral annulus fibrosus under fluoroscopic guidance. By way of a non-limiting example, the composition for regeneration may comprise, consist essentially of, or consist of 1-5 cc BMAC, 0.1-20 mm$^3$ chondrocyte nucleus material and scaffolding and 0.5 cc-5 cc PRP or PPP. Optionally, one may use a biologic scaffold made from the patient's own plasma to treat the annulus fibrosus and nucleus pulposus of the recipient disc levels(s) and the donor disc level as well. In some embodiments, the scaffold for disc regeneration may comprise, consist essentially of or consist of one or more, if not all, of PRP or PPP hyaluronic acid, fibrin glue that may for example be formed from fibrinogen and thrombin, and a flowable wound matrix, such as is available from Integra or Matristem. The scaffolding may comprise, consist essentially of or consist of one or more if not all of the following: Type I collagen, Type II collagen, proteoglycans, and glycosaminoglycans. To obtain the scaffolding, one may for example, begin with 5-20 pieces, e.g., 10 pieces of approximately 0.5-2.5 mm$^3$ e.g., 1 mm$^3$ in size, morselize them and combine with 0.1-2 cc sterile saline, e.g., 0.5 cc sterile saline with antibiotics. In some embodiments, 1-4 cc or 2-3 cc of scaffolding is inserted.

As noted above, in addition to generation of platelet rich plasma from blood for the composition for regeneration, the centrifugation process will result in the formation of two additional strata. The platelet poor plasma from that strata may be used a stem cell scaffold, and also may be effective at reducing pain. The platelet poor plasma's ability to act as a scaffold is due to the presence of a network of concentrated proteins. Beneficially, the scaffold is an autologous degradable scaffold that can hold together and support bone-marrow-derived mesenchymal stem cells and/or adipose-derived perivascular stem cells.

The fibrinogen may be used as a fibrin sealant, and the fibrinogen may be converted to fibrin by the use of thrombin. The resulting thrombin clot that is formed is used as a sealant in order to fill degenerative annular tears and to seal a stem cell introduction site or herniated disc annulotomy site. Thus, the fibrinogen may also be part of the scaffold.

The scaffold may serve one or more of the following functions: (1) to provide a matrix for stem cells to integrate/engraft during tissue transplantation; (2) to provide a platform for cell differentiation and cell to cell signaling; (3) to provide an osmotic pump to restore extracellular matrix hydration; (4) to fill gaps/tears in disc structure in order to restore/normalize disc function; and (5) to stabilize disc integrity.

PP/RP Treatment of Disc Annulus

In order to regenerate a disc, preferably one re-establishes the hydraulic effect of the disc. Using a scaffold, one can essentially seal the disc and thereby re-establish high intradiscal pressures. Accordingly, to the annulus fibrosus of the recipient disc level, one may apply PP/RP in order to heal annular tears and to fill defects/tears. Application may for example be to an epidural or a facet joint region.

When treating the disc annulus fibrosis with PP/RP, one may inject the PP/RP into any area of the annulus fibrosus for example, the posterior, posterolateral or anterior regions. This may be done with or without a scaffold comprising, consisting essentially of, or consisting of $CaCl_2$, hyaluronic acid, BMP, hydrogel, PLGA or poly (lactic-co-glycolic acid). In one embodiment, the PP/RP may be combined with calcium chloride at a ratio of 0.90-0.99 cc (e.g., 0.05 cc) PP/RP to 0.10-0.01 cc (e.g., 0.05 cc) of coagulant solution (e.g., 10% $CaCl_2$+5000 IU thrombin). Optionally, there is also a radiopaque dye.

Treatment of Donor Disc

Optionally, one may apply BMAC and PP/RP to the donor disc level in order to cause regeneration at the site from which the chondrocytes were taken. Because the donor disc level already has healthy discs, the BMAC and PP/RP do not need to have been combined with chondrocytes prior to introduction. Applications may be made to the disc nucleus and annulus in order to reduce the chance of iatrogenic degeneration and to maintain high intradiscal pressure within the normal disc by sealing the annulus within the scaffold.

As persons of ordinary skill in the art recognize, based on the foregoing, either one or both of the recipient disc level and donor disc level may be treated: (1) with or without hemoconcentration of BMAC; (2) with or without decompression of nucleus pulposus; (3) with our without injection of regenerative cells into nucleus pulposus and annulus fibrosus; (4) with our without scaffold; (5) with or without sealing of the annulus; and (6) with our without donor disc cell transplantation.

Additional Adjuncts

The mixtures that are used to treat the degenerated disc or the donor disc may also comprise one or more of the following: (1) genipin to augment disc repair; (2) simvastatin (Zocor) to prevent disc degeneration; (3) glucosamine/chondroitin sulfate/DSMO to restore the disc; (4) extracellular matrices including basement membrane matrices such as matristem to replace ECM and to promote healing; (5)

type I or type II collagen; (6) insulin-like growth factor-1 (IGF-1); (7) bone morphogenic protein(s); (8) fibrin microthreads for the scaffold to promote stem cell growth; (9) nanotubes to stimulate and to promote stem cell differentiation; (10) hydrogel(s); (11) LIM mineralization protein (LMP)-1 to increase aggrecan synthesis; (12) Link-N Peptide to increase proteoglycan and matrix synthesis; (13) Sox-9 to increase collagen synthesis and chondrogenesis; and (14) a scaffold that is plasma-based and contains Atelocollagen, hyaluronic acid and PEG-PLA.

Applications

Various embodiments of the present invention can be used in connection with laser neurotomy/rhizotomy. These techniques serve to ablate small pain fibers and/or to reduce facet arthritis pain.

Various other embodiments of the present invention can be used in conjunction with facet joint thermal ablation. These techniques can be used for one or more of the following purposes: (1) to ablate terminal facet joint nerve branch networks with a joint capsule; (2) to stimulate capsule regeneration; and (3) to provide an outside-in ablation of intercapsular synovitis.

Additionally, various embodiments of the present invention may be used in conjunction with a transforaminal epidural application. This application of stem cells may serve one or more of the following: (1) to provide regenerative cells to posterior posterolateral disc annulus and anterior facet joint capsules; (2) to reduce inflammation in the posterior/posterolateral disc, epidural space and anterior/medial facet joint capsule; (3) to reduce pain that originates from the posterior/posterolateral disc, epidural space and anterior/medial facet joint capsules; and (4) to reduce radicular pain and inflammation from the existing nerve and traveling nerve of the level of application.

Preferably for a period of at least two years (unless contraindicated) following application of the methods described herein, a subject undergoes lumbar traction, whole body vibration and/or inversion. Additionally or alternatively, the patient receives oral glucosamine and chondroitin sulfate for a period of at least two years. Still further, and unless contraindicated, in some embodiments, for a period of at least two years, the subject takes zinc supplements, such as those available over the counter. An example of a dose of zinc is 50 mg.

Any of the features of the various embodiments described herein can be used in conjunction with features described in connection with any other embodiments disclosed unless otherwise specified or implicit from context.

EXAMPLES

Example 1: Method of Regenerating Discs (prophetic)

1. Provide a patient with an IV that contains a prophylactic antibiotic.
2. Obtain platelet rich plasma and platelet poor plasma
    a. Draw 60 cc of peripheral blood. One may draw venous blood into a syringe that contains an anticoagulant.
    b. Centrifuge the blood in order to separate layers of blood tissue and to isolate blood plasma.
    c. Separate blood plasma via syringe aspiration into platelet rich plasma and platelet poor plasma.
    d. Optionally lyse platelet rich plasma platelet membrane into a lysate.
3. Isolate Mensenchymal Cells
a. Option A: From bone marrow
    (i) Optionally, sedate patient, e.g., oral or general (in some embodiments, the patient is not sedated)
    (ii) Harvest bone marrow
        1. Option 1: Pelvis
            a. Make appropriate size skin opening over anterior and/or posterior, right and/or left ilium bones;
            b. Insert a medium to large bone cannula into depth of ilium;
            c. Aspirate 2-7 cc of bone marrow into a syringe that is pre-filled with an anticoagulant;
            d. Rotate the syringe and repeat aspiration(s);
            e. Change the depth and repeat aspirations(s);
            f. Harvest 60-500 cc of bone marrow per ilium;
            g. Upon completion, hold pressure to control bleeding from bone.
        2. Option 2: Vertebra
            a. Insert a medium to large bone cannula into vertebral body, via left and/or right transpedicular approach or posterior oblique approach;
            b. Aspirate 2-7 cc of bone marrow into a syringe that is pre-filled with an anticoagulant;
            c. Rotate the syringe and repeat aspiration(s);
            d. Change the depth and repeat aspiration(s);
            e. Harvest 20-400 cc or 50-100 cc of bone marrow per side;
            f. Upon completion, hold pressure to control bleeding from bone.
    (iii) Process bone marrow
        1. Place bone marrow into centrifuge tube/bucket
        2. Run single or multiple centrifugation cycles for 9-30 minutes at 2000-4000 RPM or 2500-3500 RPM
        3. Aspirate mesenchymal tissue layer into treatment syringe.
    (iv) Ready bone marrow cells for treatment by placing into a pre-heparinized syringe after being concentrated.
b. Option B: From Adipose Tissue
    (i) Sedate patient orally, with IV sedation, with general anesthesia
    (ii) Harvest adipose tissue
        1. Option 1: Lipoaspiration
            a. Under sterile conditions, infiltrate abdominal or flank area with conventional mixture of local anesthetic and epinephrine;
            b. Infiltrate subcutaneous region with saline via a low pressure infiltration pump;
            c. Use micro cannulas; harvest 20-500 cc or 50-100 cc lipoaspirate;
            d. Isolate adipose derived stem cells via the following steps
                i. Remove fat layer from top of sample,
                ii. Wash sample to remove local anesthetic and epinephrine,
                iii. Digest with collagenase or emulsify with lecithin to remove fat tissue from stromal fraction, and
                iv. Centrifuge to form a stem cell pellet;
            e. Optionally, segregate a small aliquot of sample for cell counting and microscopy for research purposes;
            f. Sample filtration with 40-70 micro nylon cell strainer;
            g. Optionally, i. Combine isolated stem cells with platelet rich plasma
   ii. Sequestor antibodies via IgG magnetic beads
   iii. Activate stem cells via light
  2. Option 2: Mechanically
   a. Ex vivo
    i. Harvest lipoaspirate as described above or via direct excision;
    ii. Cavitate lipoaspirate to break down lipid from SVF (e.g., using ultrasonic laboratory devices such as from Hielscher);
    iii. Centrifuge stem cell pellet;
    iv. Follow steps (e)-(g) under lipoaspirate technique.
   b. In vivo
    i. Cavitate ultrasonically and process stem cell pellet;
    ii. Place a vacuum device over an abdominal or flank region;
    iii. Aspirate fat;
    iv. Process stem cell pellet.
 4. Ready stem cells in a syringe that was prewashed with an anticoagulant.
 5. Ready platelet rich plasma in a second syringe prewashed with anticoagulant.
 6. Ready P platelet rich plasma in a third syringe prewashed with anticoagulant.
 7. Harvest disc chondrocytes from a spinal level that is not in need of regeneration or from the sacrum.
  a. Option A: Donor Spinal Disc
   (i) Approach intervertebral disc either percutaneously or open transpedicular or intraspinal.
   (ii) Harvest nucleus and/or annulus tissue from intervertebral disc.
  b. Option B: Sacral Disc
   (i) Approach S1 sacral disc, percutaneously, or through an open approach transpedicular or through a trans S1 approach.
   (ii) Harvest nucleus and/or annulus tissue from sacral disc.
 8. Inject autologous mensenchymal stem cells, and optionally platelet rich plasma and optionally platelet poor plasma, into donor disc site including annulus. Optionally, inject platelet poor plasma or hyaluronic acid or fibrin glue or flowable wound matrix into the recipient disc lysate or cytokines or platelet rich plasma into the posterior and/or posterolateral disc annulus.
 9. Remove donor disc material (chondrocytes and scaffold) for transportation.
 10. Morselize disc tissue in small aliquot of saline using a scalpel or other mechanical methods, optionally, in conjunction with an extrusion step.
 11. Treat target disc with laser, either unilateral or bilateral. For example, one may use an intradiscal Holmium:YAG or Erbium laser treatment using a non-ablation setting for micro/nano pore formation, disc chondrocyte activation and proliferation.
 Optionally, steps 8 and 10-11 may be performed outside of the body.

Example 2: Harvesting Bone Marrow for Stem Cell Processing (Prophetic)

Using a Jamshidi needle, harvest 60-400 cc of bone marrow from the iliac crest. Place the bone marrow into a syringe with an anticoagulant, e.g., ACD. Process the bone marrow into bone marrow aspirate. The formation of bone marrow aspirate concentrate from bone marrow may, for example, be performed by Celling Biosciences (Spine Smith).

Optionally, one concentrates BMAC with, for example, a hemoconcentrator. When generating BMAC from bone marrow, there is a reduction of volume by 80-95%. Thus, for every volume of bone marrow, one gets 5-15% of that volume of BMAC. By way of example, 60 cc of bone marrow yields approximately 6 cc of BMAC. The Hemoconcentrator can concentrate this volume by approximately 40-60% (e.g., 50%) to 1-4 cc or 2-3 cc, e.g., approximately 3 cc.

I claim:

1. A process for creating a composition for disc regeneration, said process comprising:
 (a) morselizing donor disc material, wherein the donor disc material comprises healthy cells obtained from a non-degenerative level of a spine of a person in need of disc regeneration;
 (b) extruding the donor disc material to form an extruded material that comprises chondrocytes and an extracellular matrix;
 (c) sequestering platelets from whole blood or bone marrow in order to obtain platelet rich plasma;
 (d) extracting and concentrating the platelets from the platelet rich plasma into a platelet lysate through a cell membrane lysis procedure that uses at least one of thrombin and calcium chloride; and
 (e) mixing the chondrocytes, the extracellular matrix, a bone marrow aspirate from the person, and the platelet lysate, wherein the bone marrow aspirate comprises stem cells, to form a composition for disc regeneration wherein the composition for disc regeneration is a mixture, wherein the mixture comprises growth factors and within the mixture there is socialization between the chondrocytes and the stem cells due to cell-to-cell signaling, thereby initiating differentiation of the stem cells into chondrocytes.

2. The process according to claim 1, wherein the bone marrow aspirate comprises red blood cells.

3. The process according to claim 1, wherein step (e) further comprises mixing thrombin and calcium chloride with the chondrocytes, the extracellular, the bone marrow aspirate and the platelet lysate.

4. The process according to claim 1, further comprising photoactivating the stem cells.

5. The process according to claim 1 further comprising combining the composition for disc regeneration with a biologic scaffold, wherein the biologic scaffold comprises at least one substance selected from the group consisting of platelet poor plasma, hyaluronic acid, fibrin glue and a flowable wound matrix.

* * * * *